(12) United States Patent
O'Hare et al.

(10) Patent No.: US 6,391,823 B1
(45) Date of Patent: May 21, 2002

(54) SEPARATION PROCESS (75) Inventors: Dermot Michael O'Hare, Oxford; Andrew Michael Fogg, Manchester, both of (GB)

(73) Assignee: Isis Innovation Limited, Summertown (GB)

( * ) Notice: Subject to any disclaimer, the term of this patent is extended or adjusted under 35 U.S.C. 154(b) by 0 days.

(21) Appl. No.: 09/530,811
(22) PCT Filed: Nov. 6, 1998
(86) PCT No.: PCT/GB98/03326
  § 371 Date: May 5, 2000
  § 102(e) Date: May 5, 2000
(87) PCT Pub. No.: WO99/24139
  PCT Pub. Date: May 20, 1999

(30) Foreign Application Priority Data

Nov. 8, 1997 (GB) .............................................. 9723588
Aug. 6, 1998 (GB) .............................................. 9817022

(51) Int. Cl.$^7$ .......................... B01J 20/00; C07C 51/42; C07C 63/04
(52) U.S. Cl. ......................... 502/414; 502/80; 562/485; 562/493
(58) Field of Search ................................ 562/485, 593, 562/493; 502/80, 414

(56) References Cited

U.S. PATENT DOCUMENTS 4,096,231 A  *  6/1978  Ebert et al.
4,812,245 A  *  3/1989  Burba, III et al.
5,202,295 A  *  4/1993  McCauley

FOREIGN PATENT DOCUMENTS

EP   0 103 034    *  3/1984
JP   06-087765    *  3/1994

OTHER PUBLICATIONS

"Anion–Exchange Reactions of Layered Double Hydroxides" Martina Meyn, Klaus Beneke, Gerhard Lagaly. Inorganic Chemistry vol. 29, No. 26 pp5201–5207 (1990).*
"Selective Solid–State Interaction of cis–trans Isomers into Montmorillonite" Makoto Ogawa, Masahiro Hirata, Kazuyuki Kuroda, Chuzo Kato. Chemistry Letters pp365–368 (1992).*
"Anion–Exchange Reactions of Hydroxy Double Salts" Martina Meyn, Klaus Beneke, Gerhard Lagaly. Inorganic Chemistry vol. 32 pp 1209–1215 (1993).*
"Anion Exchange in Lithium Aluminate Hydroxides" Prabir K. Dutta and Micki Puri. Journal of Physical Chemistry vol. 93 pp 376–381 (1989).*

* cited by examiner

Primary Examiner—Paul J. Killos
Assistant Examiner—Zachary Tucker
(74) Attorney, Agent, or Firm—Volpe and Koenig, P.C.

(57) ABSTRACT

A process for separating a compound from a mixture of different compounds is disclosed for compounds comprising at least two negatively charged groups connected by a linker group. The process comprises treating the mixture with a material comprising layers containing at least two different types of cation disposed in an ordered arrangement within each layer, such as layers of formula $LiAl_2(OH)_6^+$, in order to separate the compound from the mixture by selective intercalation of the compound into the material.

30 Claims, 3 Drawing Sheets

SEPARATION PROCESS

This invention relates to a process for separating a compound from a mixture of different compounds.

BACKGROUND OF THE INVENTION

Processes for separating compounds from mixtures are of great importance, both in the laboratory and on an industrial scale. The purity of chemical compounds is dictated to a large extent by the purification step in which a compound is separated from other products of the reaction in which it is produced. The separation of a compound from its isomers, such as its regio and geometric isomers, can be particularly difficult to achieve. Conventional methods for separating a compound from its isomers include crystallisation and chromatography but these techniques can be relatively costly and time consuming and they do not always provide a sufficiently high degree of separation.

Layered double hydroxides are a class of compounds which comprise two metal cations and have a layered structure. A brief review of layered double hydroxides is provided in *Chemistry in Britain*, September 1997, pages 59 to 62. The hydrotalcites, perhaps the most well-known of the layered double hydroxides, have been studied for many years.

It is known that certain organic species may be intercalated into the layers in some layered double hydroxides and into clays. For Example, Ogawa et al., in *Chemistry Letters*, 1992, no. 3, p. 365–368, describe the intercalation of maleic and methylmaleic acids into the clay montmorillonite in a solid state reaction. The geometrical isomers of the acids, fumaric and methylfumaric acids, were not intercalated in the solid state reaction. However, when an ethanolic solution of the two isomers was used, the montmorillonite showed no selectivity and both isomers were intercalated.

The structure of the layered materials $[LiAl_2(OH)_6]X$, where X is Cl, Br or $NO_3$, and their hydrates has been described by Besserguenev et al., in *Chem. Mater*, 1997, no. 9, p. 241–247. The materials can be produced by the reaction of gibbsite $[\gamma\text{-}Al(OH)_3]$ or other forms of $Al(OH)_3$, such as bayerite, nordstrandite or doyleite, with lithium salts of formula LiX. The materials can also be formed in other ways, such as by direct precipitation (see, for example, Serna et al, *Clays & Clay Minerals*, (1997), 25,384). The structure of the $LiAl_2(OH)_6^+$ layers in the compounds is unusual amongst layered double hydroxides since it is based on an ordered arrangement of metal cations within the layers.

The synthesis of $LiAl_2(OH)_6^+$ compounds is described in U.S. Pat. No. 4,348,295 and U.S. Pat. No. 4,348,297. The use of the materials for separating hydrocarbons and for gas chromatograph columns is taught in U.S. Pat. No. 4,430,097 and U.S. Pat. No. 4,321,065, respectively. In both of these latter two documents, the technology described does not involve intercalation chemistry but surface interactions with the stationary phase i.e., liquid-solid or gas-solid interactions.

Intercalates of compounds of formula $LiOH.2Al(OH)_3$ are described in U.S. Pat. No. 4,727,167 and U.S. Pat. No. 4,812,245. Both documents relate to uses of the intercalates as additives to organic materials such as mineral oils.

A few other layered double hydroxides having cation ordering are known. The layered double hydroxide $[Ca_2Al(OH)_6]_2^+SO_4^{2-}$ is an example.

Any improvement in the degree of selectivity or efficiency of a separation process can lead to increased purity of a product and, potentially, significant cost savings. The present invention provides a separation process which can be operated under very mild conditions and is highly selective. It also has the advantage of, in some cases, having a selectivity which is solvent and/or temperature dependent and can therefore be tuned towards a particular compound in a mixture. The process is based on the use of layered materials.

SUMMARY OF THE INVENTION

Accordingly, the present invention provides a process for separating a compound from a mixture of different compounds, the compound comprising at least two negatively charged groups connected by a linker group, which process comprises treating the mixture with a material comprising layers containing at least two different types of cation disposed in an ordered arrangement within each layer, in order to separate the compound from the mixture by selective intercalation of the compound into the material. The compound may be recovered from the intercalate formed with the material.

The layered material used in the process of the present invention contains different cations within each layer in an ordered arrangement i.e., it has cation ordering. Ordered (i.e., non-random) arrangements of cations are believed to be a major factor in the selectivity of the process. The different types of cations may be cations of different metals or cations of the same metal having different oxidation states. Preferred layered materials are compounds containing layers of formula $LiAl_2(OH)_6^+$ or $Ca_2Al(OH)_6^+$ with the former being particularly preferred. However, other materials containing layers having cation ordering, such as other ordered layered double hydroxides, may be expected to be useful in the process of the invention.

The compound which is separated from the mixture by intercalation into the layered material can be readily recovered by treatment of the material with an anion which intercalates between the layers in the material in preference to the compound, thereby displacing the compound. Suitable anions for this purpose include inorganic anions such as carbonate and sulphate, for example, although anions which intercalate more or less strongly than carbonate can be used. Carbonate is preferred in most cases on account of its strong capacity for binding with the material which allows the guest (i.e., intercalated) compound to be recovered substantially quantitatively and since it potentially allows the material to be regenerated by calcining the carbonate intercalate and hydrating the resulting product. Typically, treatment of the material with carbonate to recover the compound may involve treating the material with an aqueous solution of a soluble carbonate salt (e.g., sodium carbonate) at about or above room temperature for up to several hours (e.g., at 20 to 80° C. for from 1 to 20 hours).

The intercalated compound may also be separated from the layered material in other ways. For example, the material, with the compound intercalated, may be treated in such a way as to break down the material and thereby free the compound (e.g., by treatment with a mineral acid). Alternatively, the intercalated compound may be removed by gradually protonating one or more of the negatively charged groups of the intercalated compound such that its retention within the material becomes energetically less favoured. Therefore, a further embodiment of the invention involves the recovery of the compound from the material by a method which comprises treatment with an acid under conditions which cause protonation and de-intercalation of the compound whilst leaving the layers of the material substantially intact.

The fact that the compound can be recovered from the material has clear advantages. Firstly, it allows the material to be regenerated, as mentioned above. Secondly, it means that a mixture of two compounds can be separated to provide each compound alone. For instance, a hypothetical mixture of A and B can be treated with the material to remove A from the mixture by intercalation into the material to leave behind B. The material with A intercalated is then removed from B, for example by filtration, and is treated with an anion, such as carbonate, to release A which can be readily separated from the carbonate intercalate of the material, for example by filtration. Alternatively, A could be released from its intercalate with the material by breaking down the material (e.g., by treatment with aqueous acid) and extraction of A into an organic solvent in a conventional biphasic extraction method.

The process of the invention preferably involves the treatment with the layered material of a solution of the mixture containing the compound to be separated. Suitable solvents are those which dissolve the compound. The solvents may be aqueous or non-aqueous (e.g., polar, organic solvents such as THF or acetonitrile) but, when non-aqueous solvents are used, it is preferred that they are used as mixtures with water (e.g., THF containing 10% water). The nature of the solvent can be important to the selectivity of the process. For example, when the process is used to separate a mixture of isomers, it has been found that the nature of the solvent can affect which isomer is intercalated with one isomer intercalated in some solvents and another intercalated in others.

The temperature at which the process is carried out may also affect the selectivity of the process and it has surprisingly been found that different compounds may be preferentially intercalated from the same mixture at different temperatures. Preferably, the process is carried out at temperatures from 0° C. up to the boiling point of the solvent, more preferably 20° C. to 100° C. Temperatures of below 0° C. may be employed with certain solvents having low freezing points, although the low rates of intercalation at the lower temperatures may not always provide a practically effective process.

The fact that the temperature and/or the solvent system used in the process can influence its selectivity can be used to target a particular compound for separation. Also, it means that the same material can be used to separate different compounds from the same mixture simply by varying the solvent and/or the temperature. Suitable temperatures and solvents for particular separations can be readily determined by routine experimentation in each case. Therefore, the process of the invention may involve selection of the solvent system and/or temperature so as to optimise the intercalation of the compound into the material.

The intercalation of the compound into the material can be complete in about 30 minutes to 2 hours at room temperature.

In order to effect intercalation, a solution of the mixture may be passed through the material. Conventional chromatographical and filtration techniques can be used for this purpose. For example, the layered material can be provided as a chromatographic column. The layered material may be used in the column as such or together with a support (e.g., the material embedded in resin beads). Addition of a mixture to the column leads to the elution of non-intercalated compound or compounds from the column with the intercalated compound retained. Eluting with an anion which intercalates in preference to the already intercalated compound de-intercalates the adsorbed compound. The column may then be reactivated (e.g., by calcination or, in the case of $[LiAl_2(OH)_6]^+$ layered materials, addition of concentrated LiCl solution or HCl solution). Alternatively, the mixture may be treated with the material in other ways such as, for example, by stirring a suspension of the material in the mixture.

The process of the invention can be used to separate a compound from one or more other structurally related or unrelated compounds having the same or different functional groups. The process of the invention has been found to be particularly suitable for the separation of a compound from a mixture of the compound and its isomers and this is, therefore, a preferred feature of the process. Preferably, the isomers are geometric isomers or regio-isomers. Mixtures of this type can be difficult to separate effectively using conventional methods. Alternatively, the isomers may be diastereoisomers or optical isomers; using materials having chiral structures, for example formed in the presence of a chiral guest template, it is possible to separate the different optical isomers of a compound. Layered materials suitable for separating optical isomers can be, for example, second stage intercalates (i.e., materials having intercalation in every other layer) which have chiral molecules (such as the anions of optically active diacids e.g., malic or tartaric acid) in every other layer; the optical isomers to be separated intercalate into the layers not already occupied by the chiral molecules.

The process of the invention may also be used in other separation processes, such as the separation of dianions from a mixture containing monoanions, for example. The dianions may be present as the minor or major component of the mixture.

The compounds intercalated into the material in the process of the invention comprise at least two negatively charged groups connected by a linker group. Since the compounds have at least two negatively charged groups (they may contain more than two negatively charged groups, but they preferably contain two), they are anionic although the anions may be formed solely for the purpose of the separation process. The negatively charged groups may be the anionic groups formed by the deprotonation of an acid, such as carboxylate ($CO_2^-$) and oxoanions of phosphorous and sulphur (e.g., phosphonate ($—PO_3^{2-}$), phosphate ($—OPO_3^{2-}$), sulphate ($—OSO_3^-$) and sulphonate ($—SO_3^-$)) or by the deprotonation of less acidic groups (e.g., alkoxide or phenolate) but are preferably carboxylate or sulphonate groups, more preferably carboxylate groups. The negatively charged groups in the compound may be the same or different. The linker group in the compounds provides connection between the negatively charged groups. The linker group may be wholly flexible (e.g., an alkylene chain) or it may have a degree of rigidity (e.g., an alkenylene chain). Preferably, the linker group provides a substantially rigid connection between the negatively charged groups to keep them at a substantially fixed distance apart. Suitable linker groups which provide a rigid connection include, for example, phenylene, naphthalene and other carbocyclic or heterocyclic, polyaromatic or non-aromatic, ring structures and 1,2-ethylene, each optionally substituted.

The process of the invention may be used to separate a wide variety of different types of compound including surfactants and biological molecules such as amino acids, sugars and polynucleotides, for example.

The process of the invention has been found to be particularly effective for the separation of the dianion of 1,4-benzenedicarboxylic acid from mixtures, for example mixtures comprising its 1,2- and 1,3-isomers and for the separation of the dianion of fumaric acid (i.e., trans-but-2-enedioic acid) from mixtures, for example mixtures comprising its cis-isomer, the dianion of maleic acid. The selectivity of materials containing layers having ordered cations in these separation processes is greater than 95% as determined by $^1$H nmr. The separation of the 1,4-benzenedicarboxylic dianion from its isomers and the separation of maleate dianions from fumarate dianions are therefore preferred features of the process. The process of the invention thus enables the separation of the isomers of benzenedicarboxylic acids to be achieved, simply by forming the dianions from the acids by treatment with an alkali at a suitable pH for deprotonation of both of the acid groups. Similarly, fumaric and maleic acids may be separated by the process of the invention following the formation of their dianions in the same way. After the separation has been achieved, the acids may be reformed by protonation, for example using a mineral acid. Suitable water soluble benzenedicarboxylate, fumarate and maleate anions, which allow the process to be carried out in aqueous solution, are provided by the disodium salts.

The process is equally effective for other separations such as the separation of 1,5- and 2,6-naphthalenedisulphonates and 1,2- and 1,3-benzenedisulphonates, for example.

The material which is used in the process of the invention may be any substance which contains layers having at least two different cations within each layer with the cations ordered within the layers. The materials must, of course, be capable of intercalating the compound to be separated. Examples of suitable materials are compounds of formula [LiAl$_2$(OH)$_6$]A, having ordered [LiAl$_2$(OH)$_6$]$^+$ layers, wherein A is OH, F, Cl, Br, I, (SO$_4$)$_{1/2}$ or NO$_3$, optionally hydrated with stoichiometric or non-stoichiometric amounts of water, such as [LiAl$_2$(OH)$_6$]Cl.H$_2$O. The anion A is generally intercalated between the layers and must be capable of being displaced by the binding of the compound between the layers.

Without wishing to be bound by theory, it is believed that the selectivity of the layered materials may stem from the differing packing energies of the guest compounds within the interlayer region and their interactions with the positively charged, ordered layers. When benzenedicarboxylate dianions or mixtures of maleate and fumarate dianions are treated with [LiAl$_2$(OH)$_6$]A, for example, experimental results show that all of the anions are initially intercalated into the layers but that the layers subsequently contract to expel substantially all of the dianions except the favoured 1,4-benzenedicarboxylate and fumarate dianions.

Figure 1:
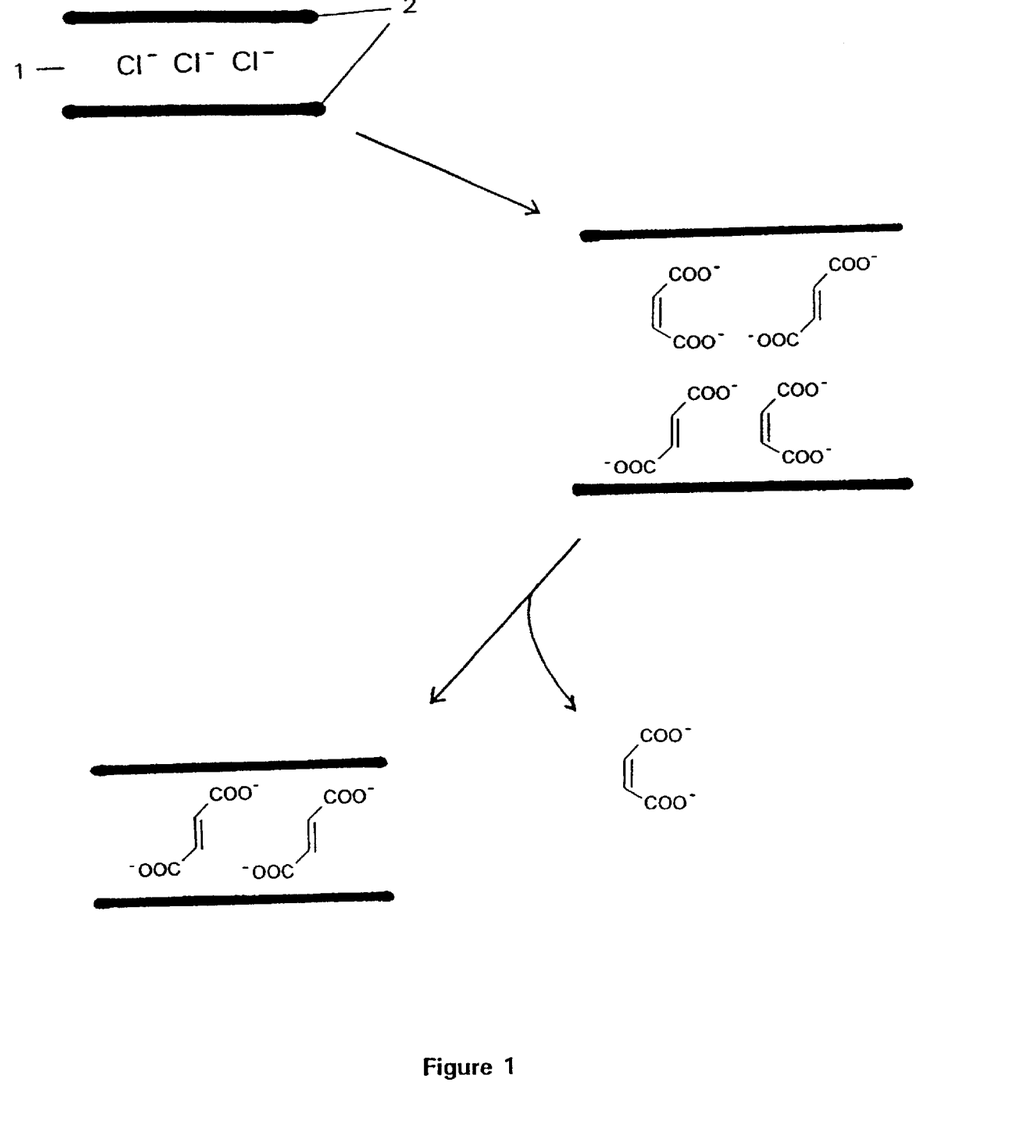
FIG. 1 shows the steps leading to the intercalation of fumarate dianions from mixtures of these dianions with maleate dianions.
Figure 2:
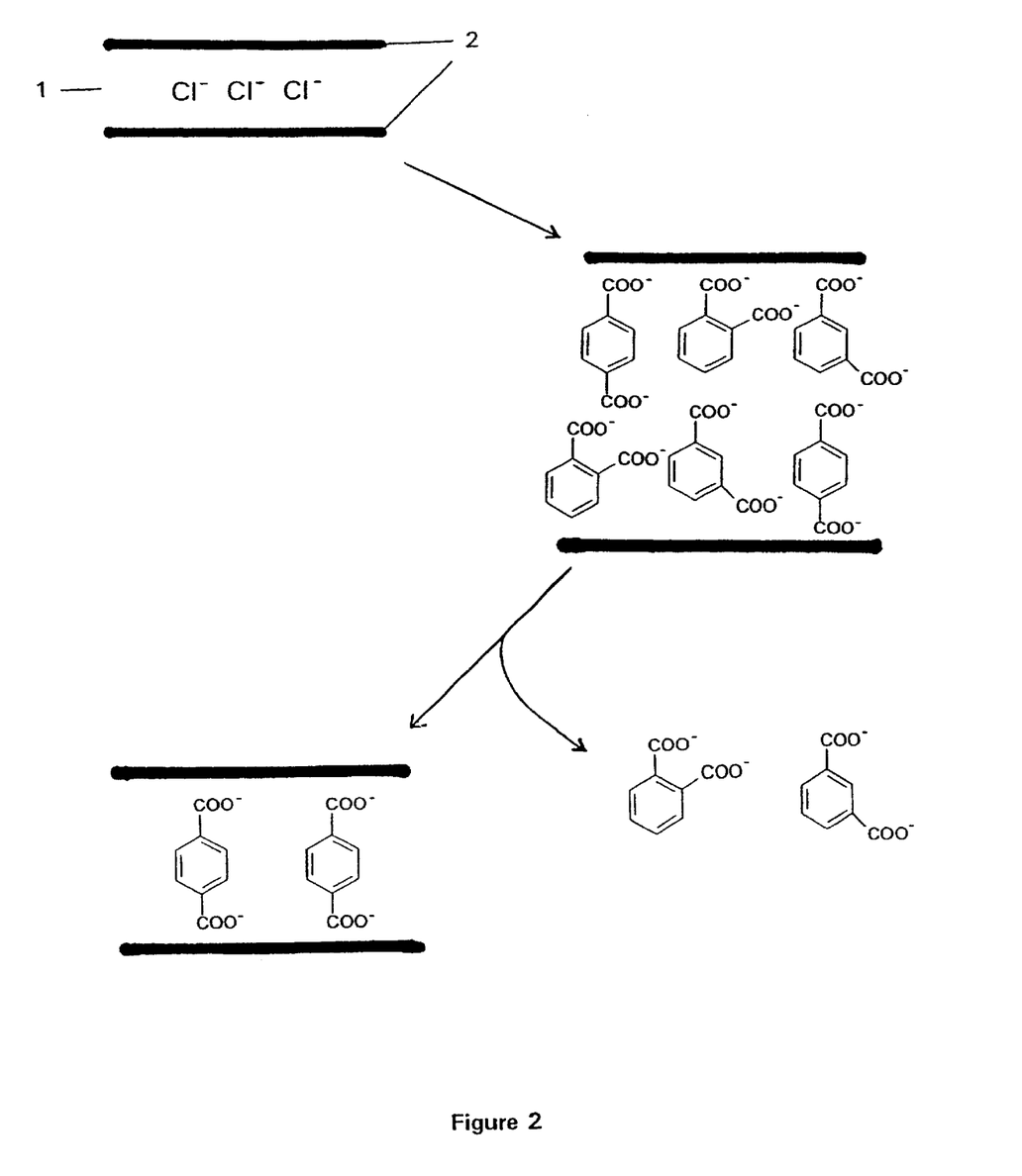
FIG. 2 shows the intercalation of 1,4-dicarboxylate dianions from mixtures containing its 1,2- and 1,3-isomers.
Figure 3:
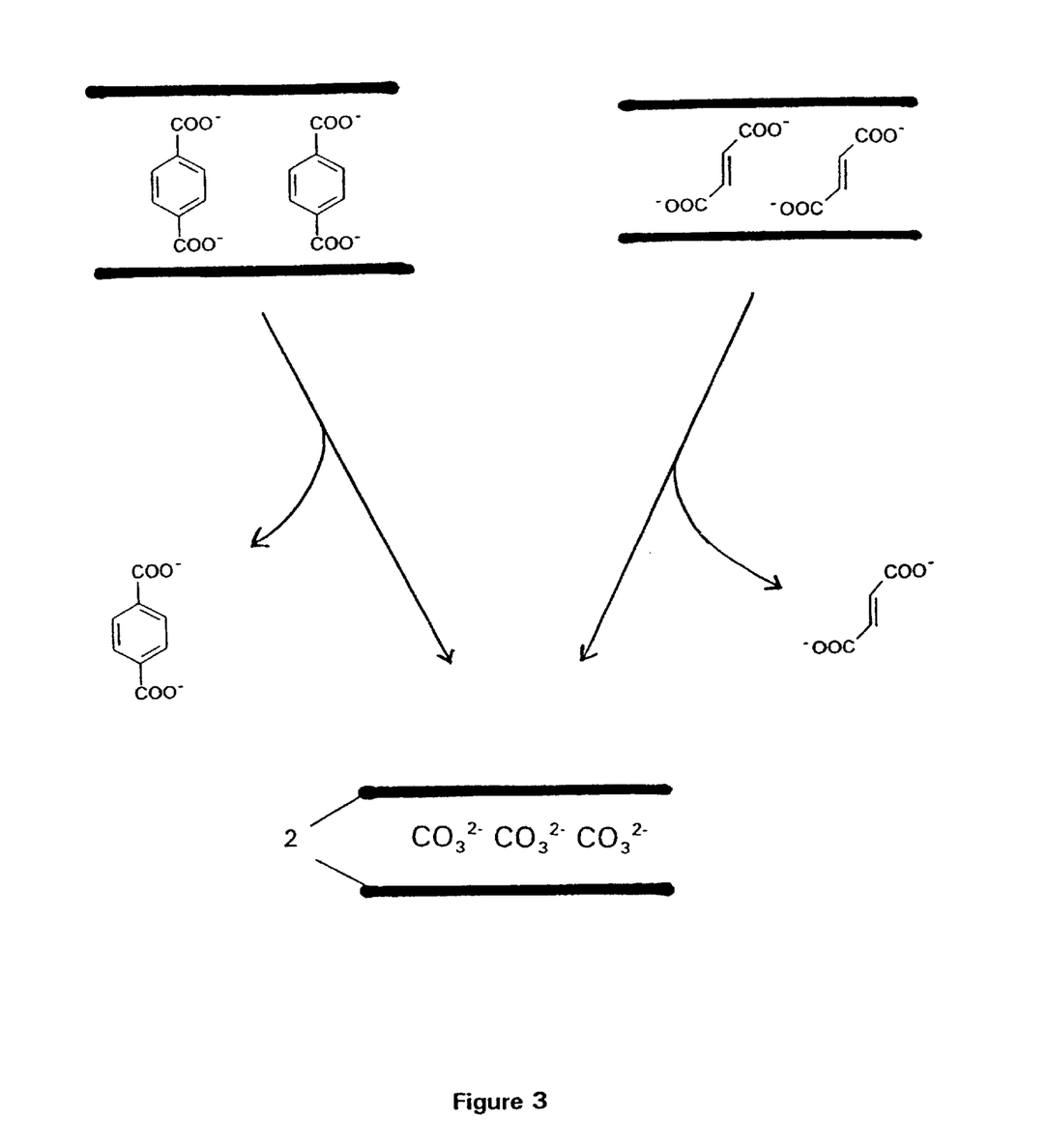
FIG. 3 shows the displacement of 1,4-dicarboxylate dianions and fumarate dianions from their intercalates with the layered material using carbonate ions.

FIGS. 1, 2 and 3 show, schematically, what is believed to be the mechanism underlying the separation process of the invention.

Referring to FIG. 1, when [LiAl$_2$(OH)$_6$]Cl.H$_2$O (1) is treated with equimolar mixtures of maleate and fumarate dianions, an increase in the layer spacing from 7.65 Å to 12.8 Å is initially observed, suggesting that all species are initially intercalated without significant selectivity. Layers (2) are of formula [LiAl$_2$(OH)]$_6^+$. The layer spacings then contract to 12.1 Å, as the energetically favoured fumarate dianions remain intercalated and their isomers leave the layers (2).

Similarly in FIG. 2, when compound (1) is treated with equimolar mixtures of 1,2-, 1,3- and 1,4-benzenedicarboxylate dianions in aqueous solution, an increase in the layer spacing to 15.1 Å is initially observed with a subsequent contraction to 14.3 Å as the less favoured isomers leave the layers (2).

The effect of treating the 1,4-benzenedicarboxylate and fumarate intercalates with carbonate is shown, again schematically, in FIG. 3. The dianions are released from between the layers in the material as carbonate ions are preferentially intercalated.

The layer spacings given in FIGS. 1, 2 and 3 were measured using X-ray diffraction techniques.

The process of the invention enables the separation of certain compounds having two negatively charged groups connected by a linker group with a high degree of selectivity, as measured by $^1$H nmr, which may be greater than 95%, possibly greater than 98%. Thus, substantially quantitative separation may be achieved using the process of the invention, particularly if it is carried more than once on the same sample. The process may be used for the separation of a compound from mixtures in which it is present in from relatively small to relatively large amounts, e.g., for the isolation of small amounts of a compound from a mixture or for the removal of minor amounts of impurity from a compound.

The invention will now be described with reference to the following non-limiting examples.

EXAMPLES

A. [LiAl$_2$(OH)$_6$]$^+$ Compounds

Prerarative Example

[LiAl$_2$(OH)$_6$]X.nH$_2$O, where X is Cl, Br, OH or NO$_3$ and n is roughly equal to from 1 to 2, was prepared by stirring gibbsite (Al(OH)$_3$) in an aqueous solution of LiX at at least threefold molar excess at 90° C. for 6 hours.

Example 1

Separation of Fumarate and Maleate Isomers

250 mg of [LiAl$_2$(OH)$_6$]Cl.nH$_2$O, where n is roughly equal to 1, were suspended in a 0.1M (for each isomer) aqueous equimolar solution of cis- and trans- sodium but-2-enedioate (Na$_2$C$_4$H$_2$O$_4$) and the suspension was stirred at room temperature for 1 hour. Complete reaction of the trans-isomer by intercalation into the material was indicated by the absence of any Bragg peaks from the host lattice in the X-ray diffraction patterns and of Cl in the elemental microanalysis.

The intercalated trans- dicarboxylate ions were extracted from the host lattice by suspending the $[LiAl_2(OH)_6]_2[trans-C_4H_2O_4]\cdot nH_2O$ in a 0.1M aqueous solution of sodium carbonate and stirring at 80° C. for 24 hours.

Example 2

Separation of 1,2-, 1,3- and 1,4-Benzenedicarboxylate Isomers 250 mg of $[LiAl_2(OH)_6]Cl\cdot nH_2O$ were suspended in a 0.1M (for each isomer) aqueous equimolar solution of sodium 1,2-, 1,3- and 1,4-benzenedicarboxylate $(Na_2C_8H_4O_4)$ and the mixture was stirred at room temperature for one hour. Complete intercalation of the 1,4-isomer into the material was indicated by the absence of any Bragg peaks from the host lattice in the X-ray diffraction patterns and of Cl in the elemental microanalysis.

The intercalated 1,4-benzenedicarboxylate ions were extracted from the host lattice by suspending the $[LiAl_2(OH)_6]_2[1,4-C_8H_4O_4]\cdot nH_2O$ in a 0.1M aqueous solution of sodium carbonate and stirring at 80° C. for 24 hours.

Example 3

Separation of 1,5- and 2,6-Naphthalenedisulphonates

The procedure of Example 2 was repeated at 100° C. using an equimolar mixture of 1,5- and 2,6-naphthalenedisulphonates in place of the benzenedicarboxylate mixture.

Resonances attributed to only the 1,5-isomer were seen in the $^1$H-NMR spectrum of the intercalate and Bragg reflections corresponding to only the $1,5-C_{10}H_6(SO_3)_2^{2-}$ intercalate were observed in the XRD of the product. Thus, a selectivity for the separation of the 1,5-isomer of at least 99% can be inferred.

The selectivity decreased from 99% with decreasing temperature and there was found to be a change in the selectivity below about 40° C. such that 73% of the intercalate formed at 20° C. is the $2,6-C_{10}H_6(SO_3)_2^{2-}$ intercalate.

Example 4

Separation of 1,2- and 1,3-Benzenedisulphonates

The procedure of Example 2 was repeated at various temperatures within the range 20 to 100° C. using a mixture of 1,2- and $1,3-C_6H_4(SO_3)_2^{2-}$ in place of the benzenedicarboxylate mixture.

Intercalation was selective (99% or greater at all temperatures) for the 1,2-isomer; XRD patterns showed Bragg reflections characteristic of only the 1,2-isomer and $^1$H-NMR resonances attributed to only $1,2-C_6H_4(SO_3)_2^{2-}$ were observed.

Example 5

Separation of 2,6-disubstituted Naphthalenes

The procedure of Example 2 was repeated using a mixture of $2,6-C_{10}H_6(CO_2)_2^{2-}$ and $2,6-C_{10}H_6(SO_3)_2^{2-}$ in place of the benzenedicarboxylate mixture.

Selective intercalation of $2,6-C_{10}H_6(CO_2)_2^{2-}$ was observed throughout the temperature range, increasing from 91% at 20° C. to at least 99% at 100° C. Secondary exchange with $Na_2CO_3$ was found to be ineffective for this guest dianion so anion exchange reactions were carried out in $D_2O$. The percentage of the guest intercalation was then inferred by $^1$H-NMR of the solution containing the dianions remaining after the intercalation reaction. Bragg reflections in the XRD pattern of the products do not correspond to the pure intercalate of either guest but correspond to a d-spacing between the two. This suggests an intermediate situation in which the same guest dianion is situated within a particular layer but the layers are randomly stacked with respect to each other.

Example 6

Separation of 1,2-disubstituted Benzenes

Example 5 was repeated using a mixture of $1,2-C_6H_4(SO_3)_2^{2-}$ and $1,2-C_6H_4(CO_2)_2^{2-}$.

The dicarboxylate was intercalated preferentially over the disulphonate with a temperature-independent selectivity of 70%, as determined by $^1$H-NMR of the products.

Example 7

Separation of 1,3-disubstituted Benzenes

Example 6 was repeated using a mixture of $1,3-C_6H_4(SO_3)_2^{2-}$ and $1,3-C_6H_4(CO_2)_2^{2-}$.

Again, the dicarboxylate was preferentially intercalated, this time with a temperature-independent selectivity of 90%, as determined by $^1$H-NMR of the products.

Examples 8–18

Variation of Selectivity with Temperature and Solvent

Competitive intercalation reactions were run with equimolar amounts of two guests in the solution mixture. A 50% mixture of water and THF was used in Example 17. In all other cases, the solvent was water. 300 mg of host $[LiAl_2(OH)_6]Cl\cdot nH_2O$ was stirred with an equimolar amount of each guest molecule, preserving a 2:1 guest excess. Experimental conditions and results are summarised in the table below.

Secondary exchange was carried out on the intercalated solid with a three-fold excess of $Na_2CO_3$ (410 mg) in 5 ml $D_2O$. This was stirred at 60° C. for approximately 2 hours. The filtrate is retained and the residue washed in $H_2O$ and EtOH. X ray diffraction was performed on the dry powder as a check that the original guest is fully exchanged with $CO_3^{2-}$. In cases where the guest did not fully exchange out, the reaction was repeated in the original $D_2O$ solution. NMR was performed on the filtrates and the integrals measured to determine the ratio of intercalated molecules.

The 1,5-naphthalenedicarboxylic acid (Examples 8, 9, 17 and 18) makes up a special case due to its lack of solubility. A 0.1 molar solution of the potassium carboxylic acid salt was made up by stirring the acid into a 0.2 molar KOH solution. Again 300 mg of host was used, with 13 ml of the solution and 375 mg of the 2,6-naphthalenedicarboxylic potassium salt. The reaction was then carried out as outlined above.

Examples 8 to 18 demonstrate how the selectivity of the process of the invention varies with temperature and solvent and illustrate the turnability of the process to particular compounds. It will be appreciated that where the selectivity is relatively low, an effective separation can be obtained by multiple treatments of the mixture with the layered material.

Examples 19–23

Variation of Selectivity with Temperature and Solvent Polarity

Competitive intercalation reactions using equimolar mixtures of 1,5-naphalenedisulphonate and 2,6-naphthalenedisulp honate and the host $[LiAl_2(OH)_6]Cl.nH_2O$ were performed as previously described.

A variety of other solvent systems were tried. 50:50 mixtures of water and another polar organic solvent were used as they could dissolve the di-sodium salts of the naphthalenedisulphonate anions.

| EXAMPLE | GUESTS A | B | REACTION CONDITIONS TEMP ° C. | TIME | % GUEST INTERCALATED A | B |
|---|---|---|---|---|---|---|
| 8 | 1,5-naphthalenedisulfonate | 2,6-naphthalenedisulfonate | 0 | 6 days | 48 | 52 |
|  |  |  | 20 | 24 h | 27 | 73 |
|  |  |  | 40 | 24 h | 52 | 48 |
|  |  |  | 60 | 24 h | 73 | 27 |
|  |  |  | 80 | 24 h | 79 | 21 |
|  |  |  | 100 | 24 h | 98 | 2 |
| 9 | 1-naphthalenesulfonate | 1,5-naphthalenedisulfonate | 20 | 24 h | 63 | 37 |
|  |  |  | 60 | 24 h | 58 | 42 |
|  |  |  | 100 | 24 h | 50 | 50 |
| 10 | 2-naphthalenesulfonate | 2,6-naphthalenedisulfonate | 20 | 24 h | 87 | 13 |
|  |  |  | 60 | 24 h | 82 | 18 |
|  |  |  | 100 | 24 h | 76 | 24 |
| 11 | 1,2-benzenesulfonate | 1,3-benzenedisulfonate | 20 | 2 h | 98 | 2 |
|  |  |  | 60 | 2 h | 99 | 1 |
|  |  |  | 100 | 2 h | 99 | 1 |
| 12 | 1,3-benzenedicarboxylate | 1,4-benzenedicarboxylate | 100 | 1 h | 3 | 97 |
| 13 | 1,2-benzenedicarboxylate | 1,3-benzenedicarboxylate | 20 | 1 h | 92 | 8 |
|  |  |  | 100 | 1 h | 90 | 10 |
| 14 | 2,6-naphthalenedicarboxylate | 2,6-naphthalenedisulfonate | 20 | 24 h | 91 | 9 |
|  |  |  | 60 | 24 h | 99 | 1 |
|  |  |  | 100 | 24 h | 99 | 1 |
| 15 | 1,2-benzenedicarboxylate | 1,2-benzenedisulfonate | 20 | 2 h | 68 | 32 |
|  |  |  | 60 | 2 h | 67 | 33 |
|  |  |  | 100 | 2 h | 71 | 29 |
| 16 | 1,3-benzenedicarboxylate | 1,3-benzenedisulfonate | 20 | 2 h | 91 | 9 |
|  |  |  | 60 | 2 h | 92 | 8 |
|  |  |  | 100 | 2 h | 91 | 9 |
| 17 | 1,5-naphthalenesulfonate (50% THF) | 2,6-naphthalenesulfonate | 20 | 24 h | 53 | 47 |
|  |  |  | 75 | 24 h | 62 | 38 |
| 18 | 1,5-naphthalenedicarboxylate | 2,6-naphthalenedicarboxylate | 20 | 24 h | 10 | 90 |
|  |  |  | 60 | 24 h | 3 | 97 |
|  |  |  | 100 | 24 h | <1 | >99 |

| | | GUESTS | | REACTIONS CONDITIONS | | % GUEST INTERCALATED | |
|---|---|---|---|---|---|---|---|
| EXAMPLE | SOLVENT | A | B | TEMP° C. | TIME | A | B |
| 19 | water | 1,5-naphthalene-disulphonate$^{2-}$ | 2,6-naphthalene-disulphonate$^{2-}$ | 20<br>60<br>100 | 24 h<br>24 h<br>24 h | 30<br>45<br>93 | 70<br>55<br>7 |
| 20 | 50% THF<br>50% water | 1,5-naphthalene-disutphonate$^{2}$ | 2,6-naphthalene-disulphonate$^{2-}$ | 20<br>75 | 24 h<br>24 h | 53<br>62 | 47<br>38 |
| 21 | 50% ethanol<br>50% water | 1,5-naphthalene-disulphonate$^{2-}$ | 2,6-naphthalene-disulphonate$^{2-}$ | 20<br>100 | 24 h<br>24 h | 85<br>82 | 15<br>18 |
| 22 | 50% acetone<br>50% water | 1.5-naphthalene-disulphonate$^{2-}$ | 2.6-naphthalene-disulphonate$^{2-}$ | 20<br>100 | 24 h<br>24 h | 80<br>>99 | 10<br><1 |
| 23 | 50% acetontrite<br>50% water | 1,5-naphthalene-disulphonate$^{2-}$ | 2,6-naphthalene-disulphonate$^{2-}$ | 20<br>100 | 24 h<br>24 h | 83<br>90 | 17<br>10 |

Example 24

Method for Recovering the Organic Quest Anions from the Host Lattice and Recovering the Ion Exchange Capacity for the Host Lattice

150 mg of $[LiAl_2(OH)_6]_2[1,4-C_8H_4O_4].nH_2O$ was suspended in 5 ml of 0.5M HCl(aq) in ethanol. The mixture was stirred at room temperature for 12 hours. X-Ray diffraction of the resulting solid showed that it had been largely converted to $[LiAl_2(OH)_6]Cl.H_2O$ with a small amount of the $2^{nd}$ stage intercalation compound $[LiAl_2(OH)_6][1,4-C_8H_4O_4][Cl].nH_2O$ also present.

Repetition of the experiment described above using 1.0M HCl(aq) in ethanol lead to the compete replacement of $1,4-C_8H_4O_4$ and the conversion of the solid to $[LiAl_2(OH)_6]Cl.nH_2O$ which can be used in future experiments.

The key feature of this process is that it provides an energy efficient, low temperature method for recovering the intercalated ions and simultaneously regenerating the host lattice.

B. $Ca_2Al(OH)_6^+$ Compounds

Preparative Example $Ca(NO_3)_2.2H_2O$ and $Al(NO_3)_3.9H_2O$ were mixed together in water and the solution was added drop wise to a solution of NaOH and $NaNO_3$. The resulting precipitate was stirred at 60° C. for 3 days. $[Ca_2Al(OH)_6]NO_3.nH_2O$ was characterised by X-ray powder diffraction and elemental microanalysis.

Example 25

Separation of Fumarate and Maleate Isomers 200 mg of $[Ca_2Al(OH)_6]NO_3.nH_2O$ was stirred in 5 ml of water over a period of 24 hours with a 2-fold excess of an equimolar mixture of cis and trans di-sodium but-2-enedioate (sodium maleate and fumarate respectively). The reaction was carried out at room temperature (20° C.) and 100° C. to see the effects of temperature on the selectivity of the process.

The degree of selectivity of the ion-exchange intercalation in crystalline $[Ca_2Al(OH)_6]NO_3.nH_2O$ was determined by recovering the organic guest ions by ion-exchange with $CO_3^{2-}$ ions according to the equation:

The procedure was as follows: The isolated intercalate produced in the reaction described above was stirred with a 3 fold excess of $Na_2CO_3$ in 5 ml of $D_2O$ at 50° C. overnight. The solid was collected by filtration, washed with water and checked by X-ray diffraction to see if all the original organic guests had been exchanged out of the solid. The solution was retained and studied by 1 H NMR to determine the ratio of anions present.

| | GUESTS | | REACTION CONDITIONS | | % GUEST INTERCALATED | |
|---|---|---|---|---|---|---|
| | A | B | TEMP ° C. | TIME | A | B |
| | cis-$C_4H_2O_4^{2-}$ | trans-$C_4H_2O_4^{2-}$ | 20 | 24 h | <1 | >99 |
| | cis-$C_4H_2O_4^{2-}$ | trans-$C_4H_2O_4^{2-}$ | 100 | 24 h | 83 | 17 |

Note: In contrast to the results observed here, the other host [LiAl$_2$(OH)$_6$]Cl.nH$_2$O shows no temperature dependent intercalation for cis versus trans-C$_4$H$_2$O$_4^{2-}$ in water. At 100° C. in water the intercalation preferences are also reversed between the two host materials.

What is claimed is:

1. Process for separating a compound from a mixture of different compounds, the compound comprising at least two negatively charged groups connected by a linker group, which process comprises treating the mixture with a material comprising layers containing at least two different types of cation disposed in an ordered arrangement within each layer, in order to separate the compound from the mixture by selective intercalation of the compound into the material, wherein the compound is recovered from the material by treatment of the material with an anion which intercalates into the material in preference to the compound.

2. Process as claimed in claim 1, wherein the material comprises layers of formula

[LiAl$_2$(OH)$_6$]$^+$ or

[Ca$_2$Al(OH)$_6$]$^+$.

3. Process as claimed in claim 1, wherein the anion is carbonate.

4. Process as claimed in claim 1, wherein the compound is recovered from the material by a method which comprises treatment with an acid under conditions which cause protonation and de-intercalation of the compound whilst leaving the layers of the material substantially intact.

5. Process as claimed in claim 1, wherein a solution of the mixture is treated with the material.

6. Process as claimed in claim 1, wherein the mixture comprises the compound and its isomers.

7. Process as claimed in claim 6, wherein the isomers are geometric or regio-isomers.

8. Process as claimed in claim 1, wherein the compound is a dianion and the mixture comprises one or more monoanions.

9. Process as claimed in claim 1, wherein a solution of the mixture is passed through the material.

10. Process as claimed in claim 1, wherein the linker group is phenylene, 1,2-ethylene or naphthalene, each optionally substituted.

11. Process as claimed in claim 1, wherein the negatively charged groups are carboxylate or sulphonate groups.

12. Process as claimed in claim 11, wherein the compound is the dianion of 1,4-benzenedicarboxylic acid and the mixture comprises the dianions of 1,2-benzenedicarboxylic acid and/or 1,3-benzenedicarboxylic acid.

13. Process as claimed in claim 11, wherein the compound is the dianion of fumaric acid and the mixture comprises the dianion of maleic acid.

14. Process as claimed in claim 12, wherein the dianion is prepared by deprotonation of the corresponding dicarboxylic acid.

15. Process as claimed in claim 12, wherein the compound is the dianion of a disodium salt or dipotassium salt.

16. Process as claimed in claim 12, wherein the separated compound is protonated to form the corresponding dicarboxylic acid.

17. Process for separating a compound from a mixture of different compounds, the compound comprising at least two negatively charged groups connected by a linker group, which process comprises treating the mixture with a material comprising layers containing at least two different types of cation disposed in an ordered arrangement within each layer, in order to separate the compound from the mixture by selective intercalation of the compound into the material, wherein the compound is recovered from the material by a method which comprises treatment with an acid under conditions which cause protonation and de-intercalation of the compound whilst leaving the layers of the material substantially intact.

18. Process as claimed in claim 17, wherein the material comprises layers of formula

[LiAl$_2$(OH)$_6$]$^+$ or

[Ca$_2$Al(OH)$_6$]$^+$.

19. Process as claimed in claim 17, wherein a solution of the mixture is treated with the material.

20. Process as claimed in claim 17, wherein the mixture comprises the compound and its isomers.

21. Process as claimed in claim 17, wherein the isomers are geometric or regio-isomers.

22. Process as claimed in claim 17, wherein the compound is a dianion and the mixture comprises one or more monoanions.

23. Process as claimed in claim 17, wherein a solution of the mixture is passed through the material.

24. Process as claimed in claim 17, wherein the linker group is phenylene, 1,2-ethylene or naphthalene, each optionally substituted.

25. Process as claimed in claim 17, wherein the negatively charged groups are carboxylate or sulphonate groups.

26. Process as claimed in claim 25, wherein the compound is the dianion of 1,4-icarboxylic acid and the mixture comprises the dianions of 1,2-benzenedicarboxylic acid and/or 1,3-benzenedicarboxylic acid.

27. Process as claimed in claim 25, wherein the compound is the dianion of fumaric acid and the mixture comprises the dianion of maleic acid.

28. Process as claimed in claim 26, wherein the dianion is prepared by deprotonation of the corresponding dicarboxylic acid.

29. Process as claimed in claim 26, wherein the compound is the dianion of a disodium salt or dipotassium salt.

30. Process as claimed in claim 26, wherein the separated compound is protonated to form the corresponding.

* * * * *

UNITED STATES PATENT AND TRADEMARK OFFICE
CERTIFICATE OF CORRECTION

PATENT NO.    : 6,391,823 B1
DATED         : May 21, 2002
INVENTOR(S)   : O'Hare et al.

It is certified that error appears in the above-identified patent and that said Letters Patent is hereby corrected as shown below:

Column 6,
Line 41, delete "Prerative" and insert therefor -- Preparative --.

Column 7,
Lines 40 and 63, before "[LiAl$_2$(OH)$_6$]$_2$", insert therefor -- → --.

Column 8,
Lines 12, 37 and 51, before "[LiAl$_2$(OH)$_6$]$_2$", insert therefor -- → --.

Column 10,
Line 16, delete "naphthalenedisulp honate" and insert therefor
-- naphthalenedisulphonate --.

Column 11,
Example 23, under solvent, delete "acetontrite", and insert therefor -- acetonitrile --.

Column 14,
Line 31, delete "17" and insert therefor -- 20 --.
Line 44, delete "icarboxylic", and insert therefor -- benzenedicarboxylic --.
Line 56, after "corresponding" insert therefor -- dicarboxylic acid --.

Signed and Sealed this

Twelfth Day of November, 2002

Attest:

JAMES E. ROGAN
Attesting Officer     Director of the United States Patent and Trademark Office